United States Patent [19]

Ginsburg et al.

[11] 4,413,979
[45] Nov. 8, 1983

[54] PREFORM FOR MOLDING CUSTOM DENTAL IMPRESSION TRAYS

[75] Inventors: Stephen J. Ginsburg, Ann Arbor; Frederick E. Draheim, Milford, both of Mich.

[73] Assignee: Black Knight Investments Limited, Georgetown, Cayman Islands

[21] Appl. No.: 31,665

[22] Filed: Apr. 19, 1979

[51] Int. Cl.³ .............................................. A61C 9/00
[52] U.S. Cl. ...................................... 433/41; 433/37; 433/48
[58] Field of Search .................. 433/48, 41, 40, 37, 433/38, 42, 43, 45, 47; 128/136

[56] References Cited

U.S. PATENT DOCUMENTS

| | | | |
|---|---|---|---|
| 1,406,492 | 2/1922 | Robinson | 433/45 |
| 1,509,377 | 9/1924 | Rodgers | 433/37 |
| 1,666,097 | 4/1928 | Jones | 433/45 |
| 1,979,493 | 11/1934 | Salvio | 433/38 |
| 2,035,232 | 3/1936 | Hershaw | 433/45 |
| 2,404,684 | 7/1946 | Barishman | 433/47 |
| 2,758,374 | 8/1956 | Fisher et al. | 433/37 |
| 3,064,354 | 11/1962 | Pos | 433/71 |
| 3,302,289 | 2/1967 | Spaulding | 433/214 |
| 3,303,844 | 2/1967 | Johnson et al. | 128/136 |
| 3,312,218 | 4/1967 | Jacobs | 433/37 |
| 3,473,225 | 10/1969 | Deuschle et al. | 433/48 |
| 4,161,065 | 7/1979 | Gigante | 433/214 |

Primary Examiner—John J. Wilson
Attorney, Agent, or Firm—Sherman & Shalloway

[57] ABSTRACT

A preform consisting of a planar section of a thermoplastic having a glass transition temperature a few degrees above body temperature and a softening point below about 160° F. is used to form custom, quadrant, dental impression trays. The preform is of uniform thickness except for a raised ridge, extending across both sides of the sheet, terminating in an elongated handle at one end, and dividing the preform into a pair of asymmetrical sections shaped to fit the buccal and the lingual musculature along a dental arch. The tray may be heated above its softening point and the side sections bent in a common direction about the central ridge so that their ends extend substantially parallel with one another to form a trough having a U-shaped cross-section. If the sections are bent in a first direction about the ridge a tray useful for the maxillary left or the mandibular right quadrants results; if the sections are bent in the opposite direction a tray useful for the maxillary right or the mandibular left is formed. The heat-softened preform may be placed in the patient's mouth, over a quadrant of the dental arch, and allowed to harden in the mouth to provide a custom impression tray.

10 Claims, 6 Drawing Figures

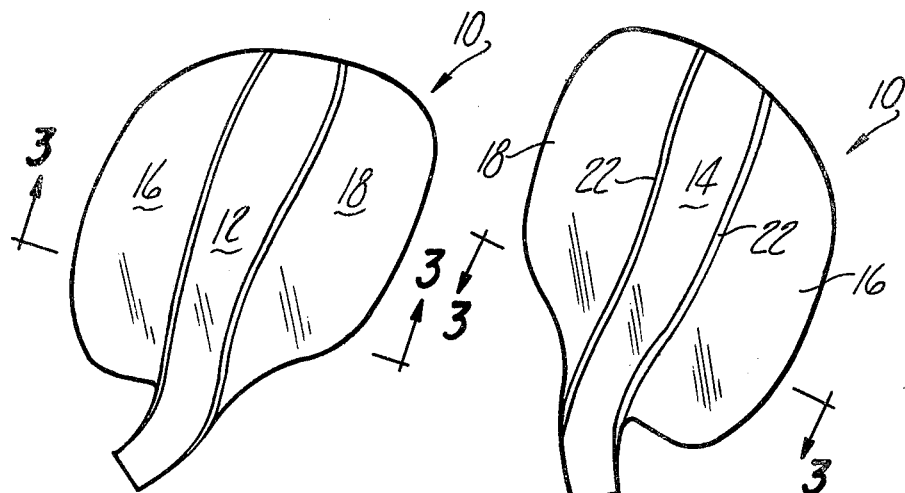
Fig-1
Fig-2
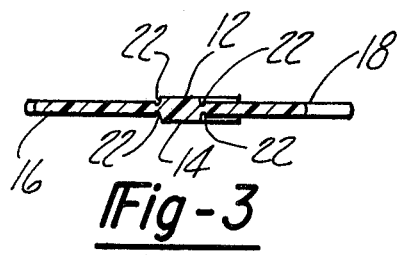
Fig-3
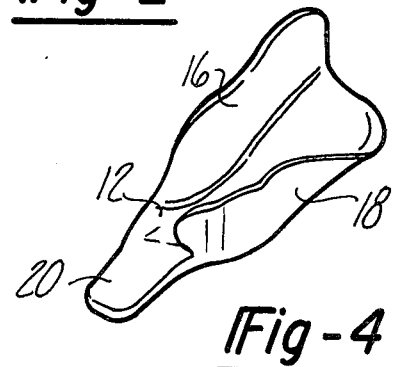
Fig-4
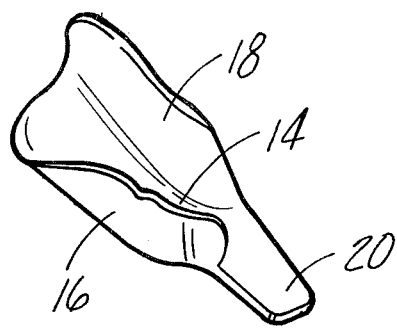
Fig-5
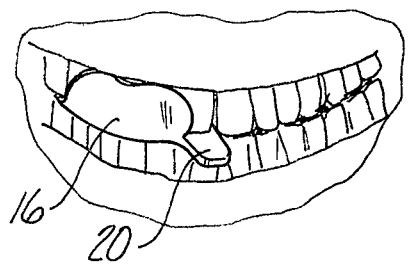
Fig-6

PREFORM FOR MOLDING CUSTOM DENTAL IMPRESSION TRAYS

BACKGROUND OF THE INVENTION

1. Field of the Invention

This invention relates to a thermally moldable preform useful for creating custom, quadrant, dental impression trays and to a method of forming trays using the preform.

2. Prior Art

As is a preliminary step to the formation of a denture, a trough-shaped impression tray is filled with a casting material and brought into contact with the section of the dental arch of which the impression is to be made. In the process of forming a sectional impression a quadrant impression tray is employed that fits over half the dental arch and has a projecting handle at its forward end. These quadrant trays are available in either a first form that may be used with either the maxillary left quadrant or the mandibular right quadrant, or a second form that may be used with either the maxillary right quadrant or the mandibular left quadrant. The appropriate tray is filled with impression material and brought into contact with a section of the dental arch to form an impression. The resultant casting is used to form a custom impression tray which closely follows the contours of the dental arch and teeth so that when it is filled with impression material a final impression may be taken having relatively constant wall thickness to equalize the pressure on all points.

Typically, the time and expertise required to form a final impression tray from the initial impression necessitates two vists or considerable waiting from the patient to the dentist; one to form the initial impression and a second to form the final impression using the final tray.

Copending patent application Ser. No. 843,433 entitled "Anatomical Intra-Orally Moldable Dental Impression Tray and Method of Using the Same" discloses a thermally moldable impression tray that may be used by a dentist to form a final impression in a single session, eliminating the delay and cost of the two-step process. The impression tray of that application is formed of a thermo-plastic having a glass transition temperature slightly above body temperature and below a temperature that would cause discomfort to the patient's mouth. The impression tray is heated above its softening temperature externally of the mouth and is then placed within the mouth and shaped to conform to the patient's oral tissue. The tray is then allowed to cool below its glass transition temperature while in the mouth. When removed and chilled to room temperature, the resultant tray has all the attributes of a custom impression tray and may be immediately used to form a final impression. The previous application discloses full impression trays of a first type for use within the mandibular section and of a second type for use with a maxillary section.

The present invention constitutes an application of the principles of that previous invention to quadrant impression trays in a novel manner that eliminates the need for provision of different forms of quadrant trays for use with different dental sections.

SUMMARY OF THE INVENTION

The present invention provides a preform of a material having the same physical properties as the materials used with the thermally moldable denture of patent application Ser. No. 843,443. The preform is a sheet of a uniform thickness with the exception of a raised ridge that extends along both surfaces to divide the preform into a pair of asymmetrical sections. The central ridge projects beyond the side sections at one end to form an elongated handle. One of the side sections has an edge contour adapted to fit the lingual musculature of the mouth while the other section has an edge contour shaped to fit the buccal tissue.

When the preform is heated above the softening temperature of the plastic, as by immersing it in heated water, the side sections may be bent in a common direction about the central ridge to create an impression tray having an approximately U-shaped cross-section. If the sections are bent in a first direction, so that their sides forming a first surface of the preform oppose one another, the resulting tray will fit two diagonally opposed dental quadrants, for example, the mandibular right and the maxillary left. If the bend is formed in the opposite direction, so that the surfaces of the sections forming the second side of the preform oppose one another, then the preform will serve for use with the opposite two quadrants, i.e., the maxillary right and the mandibular left.

The final shaping of the tray is preferably performed in the patient's mouth with the concave side of the ridge in position over the teeth of the appropriate quadrant. In this manner the side sections may be shaped into close fit with other contacting tissues.

If necessary to achieve a better fit, the preform may be trimmed while in its softened state. The preform is preferably allowed to cool below its glass transition temperature while in position in the patient's mouth so as to retain the exact desired form. Once cooled to approximately mouth temperature, the preform may be removed and used in exactly the same manner as any other custom impression tray.

The preform and the method of the present invention thus achieves the dual advantages of allowing the formation of a custom impression tray quickly, simply, and in a single sitting, and additionally allows an impression tray for any of the mouth quadrants to be formed with a single preform.

The preforms of the present invention may be made available in more than one size so that the selected preform will make a good approximate fit with the mouth of the patient.

Other objectives, advantages and applications of the present invention will be made apparent by the following detailed description of a preferred embodiment of the invention. The description makes reference to the accompanying drawings in which:

FIG. 1 is a top view of a preform made in accordance with the present invention;

FIG. 2 is a bottom view of the preform of FIG. 1;

FIG. 3 is a sectional view through the preform of FIGS. 1 and 2 taken along lines 3—3 of both FIG. 1 and FIG. 2;

FIG. 4 is a perspective view of a quadrant, custom dental impression tray for use with the maxillary left and the mandibular right quadrants formed from the preform of FIGS. 1–3;

FIG. 5 is a perspective view of the alternative form of dental impression tray which may be formed from the preform of FIGS. 1–3, useful with the maxillary right and mandibular left quadrants; and FIG. 6 is a perspective view of the tray of FIG. 4 in position with respect to a maxillary right dental quadrant.

A preform made in accordance with the present invention, as illustrated in FIGS. 1-3, constitutes a planar section, generally indicated at 10, of a thermoplastic having a glass transition temperature above human body temperature and below a temperature at which the plastic may be inserted in a patient's mouth without substantial discomfort to the patient or burning of the patient's mouth tissue. The softening temperature of the thermoplastic, i.e., the temperature at which the material may be readily manually molded, will typically be somewhat higher than the glass transition temperature and this softening temperature should also be below the temperature at which discomfort or burning may occur if the plastic is inserted into the patient's mouth. The upper limit of the glass transition temperature will typically be about 135° F. while the upper limit of the softening temperature may be slightly higher.

Thermoplastics having these physical characteristics and additionally having the proper chemical characteristics for dental use are well known and readily available.

The preform 10 is created by molding appropriate plastic components under appropriate conditions of temperature and pressure in matched molds.

The preform 10 consists of a sheet having raised ridges 12 and 14 formed on opposed sides of the sheet, directly opposite to one another, to divide the sheet into a pair of sections or flanges 16 and 18. The sections 16 and 18 are asymmetrical with respect to one another and the ridge section 12-14 extends beyond the flanges 16 and 18 at one end to form an elongated handle 20.

Grooves 22 are formed into the thickness of the sections 16 and 18 on both sides of the sheet, along opposed sides of the ridges 12 and 14. In a preferred embodiment of the invention the sections 16 and 18 may have a thickness of approximately 0.050 inches and the thickness of the preform at ridges 12 and 14 may be approximately 0.090 inches. Thus the ridges are each raised approximately 0.020 inches above the side sections. The grooves 22 may be 0.010 inches in depth.

The edge contours of the side sections 16 and 18 are such as to generally conform to the typical oral tissue on the lingual and buccal sides respectively when the preform is shaped into a completed tray as shown in FIG. 4 or 5. Accordingly, the lingual section 16 will have a contour more normal to the handle 20 than the buccal section 18.

In use, the preform 10 is heated above the softening temperature of the thermoplastic by immersion in heated water or by use of an infrared lamp or a heat blower or the like. The dentist may then bend the two side sections 16 and 18 about the central ridge section 12-14 in either of two directions, depending upon the quadrant of the patient's mouth with which the tray is to be used. The grooves 22 act as bending lines to facilitate proper shaping of the tray. The side sections may be bent in a first direction, shown in FIG. 4, so that the ridge 12 is on the concave side of the resulting U-shaped trough. This tray is useful with the maxillary left or mandibular right quadrants. Alternatively, the side sections may be bent in the opposite direction so that the ridge section 14 is on the concave side of the trough resulting in the tray of FIG. 5, useful for the maxillary right and mandibular left quadrants.

While still in its softened state the partially formed tray may be inserted in the patient's mouth in the manner illustrated in FIG. 5 so that the ridge section is in contact with the top of the teeth on the desired quadrant. The tray may then be bent into the desired final, custom shape. If trimming the tray is necessary the tray may be removed from the mouth before it is softened or it may be removed from the mouth and reheated above its glass transition temperature and trimmed with scissors or the like. The tray is then reinserted in the mouth, properly positioned and formed, and allowed to cool below its glass transition temperature while in the mouth so as to insure achievement of the desired shape.

The resulting tray is then ready for immediate use in the manner of any custom final impression tray.

The embodiments of the invention in which an exclusive property or privilege is claimed are defined as follows:

1. A dental tray for use in taking a dental impression comprising a thin planar sheet, said sheet being constructed of a material which is rigid at mouth temperature but which is pliant when heated to a predetermined temperature, and a handle protruding outwardly from one end of the sheet, wherein said dental tray is of a one-piece construction and includes a first elongated side and a second opposing, elongated side, said first and second sides extending asymmetrically from said handle, whereby said tray is reversible and can be used in taking a dental impression on all four quadrants of a human dentition.

2. A preform for use in molding custom, partial, dentulous impression trays, comprising: a sheet formed of a thermoplastic having a hardening temperature above body temperatue and below about 160° F., the sheet having a central axis with an elongated handle formed at one end of the central axis, the central axis dividing the sheet into a first section having an edge contour adapted to extend along the buccal tissue of the patient when the sheet is bent into tray form and a second section asymmetrical with respect to the first section and having an edge contour adapted to mate with the lingual area of the patient when the sheet is bent into a dental impression tray, whereby the sheet may be formed into a custom dental impression tray adapted to fit either the maxillary left and the mandibular right of the patient or the maxillary right and the mandibular left of the patient by raising the sheet above its hardening temperature, bending the buccal and the lingual sections in a common direction about the central axis, the direction in which the sections are bent controlling the type of tray formed, and cooling the resulting tray below its hardening temperature.

3. The preform of claim 2 in which the thermoplastic has a glass transition temperature above body temperature.

4. The preform of claim 2 wherein the first and second sections of the tray have substantially uniform thickness and the section of the tray along the central axis has a greater thickness so as to form raised ridges along the central axis on both sides of the preform, whereby the first and second sections may be bent about the central ridge to form the partial impression tray.

5. The impression tray of claim 2 wherein the partial section for which the preform may be formed into a custom tray constitutes a quadrant of the dental arch.

6. The preform of claim 4 including sections of reduced thickness relative to the thickness of said first and second sections, extending along both edges of the central ridge to allow easy bending of the sections about the central axis.

7. The method of forming a custom, quadrant, dentulous impression tray of either a first type which may be used with the maxillary left quadrant or the mandibular right quadrant or a second type that may be used with the maxillary right quadrant or the mandibular left quadrant, comprising: forming a planar preform of thermoplastic material having a hardening temperature above human body temperature and below about 160° F., the preform having a central axis with an elongated handle at one end, the axis dividing the preform into a pair of asymmetrical sections, one contoured to fit the buccal musculature and the other to fit the lingual musculature; heating the preform above its hardening temperature; bending both sections in the same direction, about the central axis, so that their ends extend generally parallel to one another; and cooling the formed tray below its hardening temperature.

8. The method of claim 7 in which the preform, heated above its hardening temperature, is placed in the patient's mouth with the central axis aligned over the web of the ridge and the top surface of the teeth of the quadrant of the dental arch with which it is to be employed, and after the side sections are bent the tray is allowed to cool to body temperature in this position, whereby the side sections may be shaped to a form adapted to accommodate the dental arch section.

9. The method of claim 8 in which the thermoplastic material has a glass transition temperature above body temperature and the formed preform is allowed to cool below the glass transition temperature before removal from the patient's mouth.

10. The method of claim 7 in which the section of the tray along the central axis of the tray is thickened on both surfaces, relative to the side sections, and one of the resulting ridges is brought into alignment with the top surfaces of the teeth of the dentulous ridge.

* * * * *